United States Patent [19]

El Shami et al.

[11] Patent Number: 5,470,713
[45] Date of Patent: Nov. 28, 1995

[54] METHOD AND ELEMENT FOR MEASURING ANALYTES IN BIOLOGICAL FLUIDS USING IMMOBILIZED BINDER-ANALYTE LABELED COMPLEX

[75] Inventors: A. Said El Shami, Agoura Hills, Calif.; Christopher W. Hand, Freeland, England; Susan A. Miller, Witney, England; Robert A. Moore, Noke, England

[73] Assignee: Diagnostic Products Corporation, Los Angeles, Calif.

[21] Appl. No.: 68,931

[22] Filed: May 28, 1993

Related U.S. Application Data

[60] Continuation of Ser. No. 694,471, May 1, 1991, abandoned, which is a division of Ser. No. 344,179, Apr. 26, 1989.

[51] Int. Cl.$^6$ ............................................. G01N 33/543
[52] U.S. Cl. .................... 435/7.72; 435/7.93; 435/962; 435/973; 436/501; 436/518; 436/524; 436/527; 436/528; 436/529; 436/531; 436/533
[58] Field of Search ........................ 435/7.93, 7.9, 435/6, 973, 7.72, 962; 436/501, 578, 524, 528, 531, 534, 527, 529, 533

[56] References Cited

U.S. PATENT DOCUMENTS

| 4,434,236 | 2/1984 | Freytag | 436/572 |
| 4,895,809 | 1/1990 | Schlabach et al. | 436/578 |

Primary Examiner—David A. Saunders
Attorney, Agent, or Firm—Joseph E. Mueth

[57] ABSTRACT

The method of measuring analytes in biological fluids is disclosed wherein a specific binder to a given analyte is covalently immobilized onto a solid support to which a labeled analyte is pre-reacted and stabilized to form a binder-labeled analyte complex. A sample is contacted with said immobilized complex wherein an analyte in the sample, if present, competes with the labeled analyte bound to the immobilized binder for binding sites on said binder thus displacing a given amount of the labeled analyte which is directly proportional to the amount of analyte present in the sample. The affinity of the labeled analyte to the analyte's specific binder is lower than the affinity of the unlabeled analyte to the same binder.

16 Claims, 2 Drawing Sheets

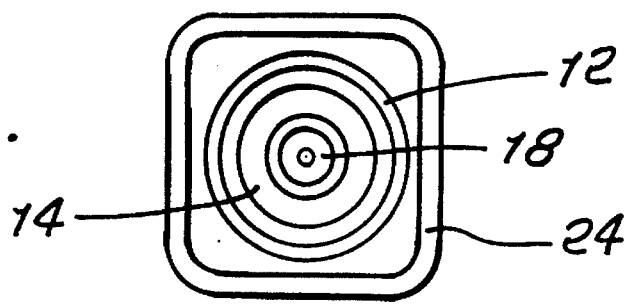
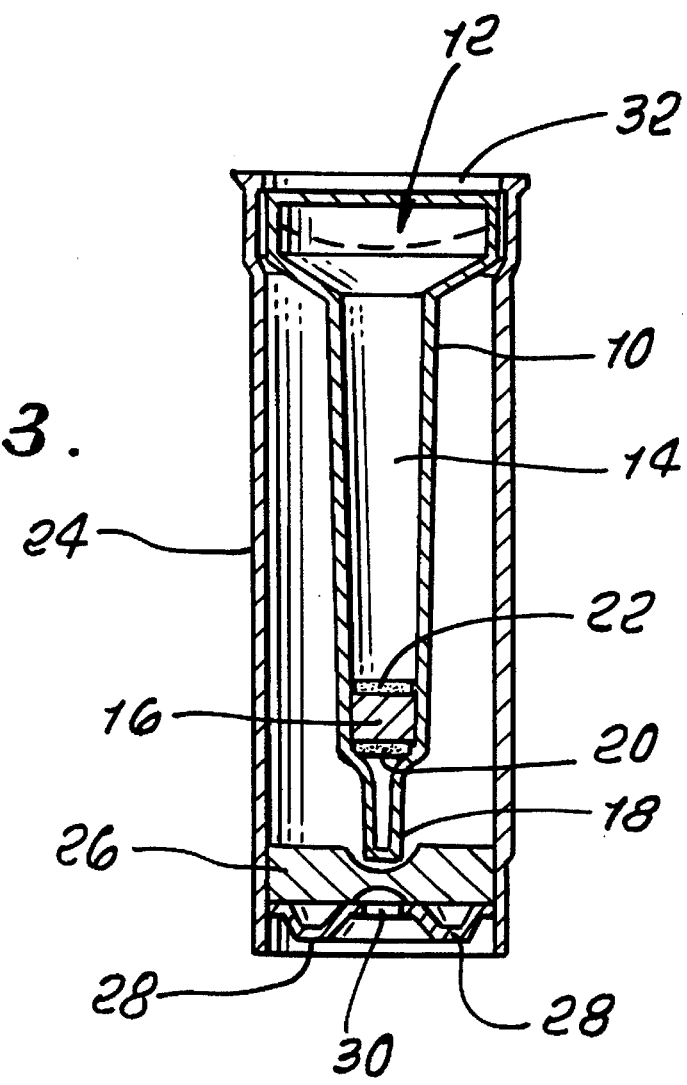

METHOD AND ELEMENT FOR MEASURING ANALYTES IN BIOLOGICAL FLUIDS USING IMMOBILIZED BINDER-ANALYTE LABELED COMPLEX

CROSS REFERENCE TO RELATED APPLICATIONS

This application is a continuation of application Ser. No. 07/694,471, filed on May 1, 1991 and now abandoned, which is a division of application Ser. No. 07/344,179, filed Apr. 26, 1989.

BACKGROUND OF THE INVENTION

Competitive isotopic and non-isotopic immunoassays or binding assays with solid phase or second antibody separations for measuring analytes in biological fluids have been described in the literature for over two decades. Numerous United States and foreign patents have been issued dealing with one or more aspects of these basic techniques.

Competitive enzyme immunoassays for various analytes were disclosed in U.S. Pat. Nos. 3,654,090 to Schurrs et al and 3,850,752 to Schurrs et al.

In enzyme immunoassays the enzyme label is prepared by one of several methods in which the analyte is covalently attached to the enzyme and the free unreacted analyte is separated from the enzyme labeled analyte either by dialysis and/or chromatography.

In such methods the free unconjugated enzyme is, in most cases, not separated from the conjugated enzyme for two practical reasons:

1. It requires tedious affinity purification and if accomplished produces a very unstable conjugated enzyme-analyte label since the latter constitutes a very low ratio of the unconjugated enzyme.
2. The analyte specific binder bound enzyme, and not the free unbound enzyme, is the fraction that is quantitated after exhaustive washing of the free unbound enzyme.

It follows, therefore, that in the aforementioned type assays the zero dose concentration has the highest signal since there is no analyte to compete with the labeled analyte for binding sites on the analyte's specific binder.

In competitive enzyme immunoassays the absence of a given analyte in a sample produces the highest color while the presence of a given analyte in a sample will produce progressively less color as compared to the zero dose depending on the concentration of said analyte in a given sample. For qualitative, "on site" type assays whereby a "yes" "no" answer is needed for the detection of a given analyte in biological fluids, the type of competitive enzyme immunoassays described in U.S. Pat. Nos. 3,654,090 and 3,850,752 are unsuitable for obvious reasons: (1) the decrease in color from a reference zero dose is difficult to detect by the naked eye, and (2) washing is required to separate the free unbound enzyme from the bound enzyme.

It is the object of the present invention to reverse such a trend since it is more logical to observe the presence of color in samples containing a given analyte while negative samples, samples devoid of a given analyte, produce no color.

U.S. Pat. No. 3,817,837 to Rubinstein et al and U.S. Pat. No. 3,852,157 to Rubinstein et al and other follow-up patents disclose homogenous type enzyme amplification immunoassay for haptens where the separation of antibody bound enzyme from free unbound enzyme is not required. In said enzyme amplification assay system the antibody-hapten enzyme labeled complex inhibits the enzyme from reacting with its substrate since the active site on the enzyme molecule is sterically hindered by the antibody to the hapten. By contacting the antibody's hapten-enzyme complex and the enzyme complex and the enzyme substrate with a sample containing a given hapten to the antibody it competes with the hapten-enzyme label for antibody sites thus allowing the enzyme to react with its specific substrate. This technique is limited to few enzymes specifically glucose-6-dehydrogenase (U.S. Pat. No. 3,875,011) malate dehydrogenase (U.S. Pat. No. 4,191,613) and U.S. Pat. Nos. 4,203,802 and 4,067,774.

U.S. Pat. No. 4,434,236 to Freytag discloses a method for the rapid determination of analytes in biological specimens by using an analyte-analogue immobilized on a solid phase wherein a displaceable labeled antibody to the analyte is found. In this disclosed method the antibody has a greater affinity for the analyte than for the analyte-analogue. The presence of an analyte in a sample specific for said antibody will easily displace the labeled antibody. Consequently, the amount of displaced labeled antibody is related to the amount of analyte present in the sample.

Although this method of U.S. Pat. No. 4,434,236 is an improvement over the previously cited patents it relies on two important factors; namely, (i) the use of an analyte-analogue that has a lower affinity to the analyte's labeled antibody, and (ii) the immobilization of analyte-analogues, especially small compounds (such as haptens), on a solid support is not easily achieved and requires specific functional groups on the analyte-analogue in order to affect immobilization. Furthermore, since the affinity of the analyte-analogue to the analyte's antibody is purposely low, the changes of labeled antibody leaking off the solid phase is quite probable.

U.S. Pat. No. 4,446,232 to Liotta, is similar in context to that disclosed in U.S. Pat. No. 4,434,236, wherein a given antigen is impregnated in a given matrix in the first zone of the disclosed device. In said matrix containing a given antigen, an enzyme-linked antibody is reacted to said antigen. In the presence of antigen in a biological specimen the antibody is displaced into a second zone which contains materials capable of reacting with the enzyme linked antibodies to produce a color. Determination of antibodies in biological fluids is also disclosed by Liotta wherein the antibody is impregnated in first zone and reacted with enzyme-linked antigen. Although this approach is a simple modification of Freytag's approach, it suffers several technical drawbacks; (1) the impregnation of antigens or antibodies in the first zone of Liotta's device will be prone to antigen or antibody "leakage" in the absence of patient antigens or antibodies, (ii) the affinity of enzyme-linked antibody or antigen is not defined. The competition between sample antigen and impregnated antigen in the first zone to the enzyme-linked antibody is by no means instantaneous because of steric hindrance and the ability of the sample antigen, like hCG in Example 1 of said patent, to dislodge the enzyme-linked antibody from the impregnated antigen is highly improbable because of steric hindrance and equilibrium considerations.

It is well established in the art that large molecules (greater than 20 kilo daltons), require longer incubations with their specific binders to reach equilibrium. When the specific antibody (molecular mass 150 kilo daltons) is linked to an enzyme (molecular mass greater than 50 kilo daltons), i.e., the effective molecular mass of the enzyme-linked antibody is approximately 200 kilo daltons, and said enzyme-linked or antigen is not defined. The competition between sample antigen and impregnated antigen in the first zone to the enzyme-linked antibody is by no means instantaneous because of steric hindrance and the ability of the sample antigen, like hCG in Example 1 of said patent, to dislodge the enzyme-linked antibody from the impregnated antigen is highly improbable because of steric hindrance and equilibrium considerations.

It is well established in the art that large molecules (greater than 20 kilo daltons), require longer incubations with their specific binders to reach equilibrium. When the specific antibody (molecular mass 150 kilo daltons) is linked to an enzyme (molecular mass greater than 50 kilo daltons), i.e., the effective molecular mass of the enzyme-linked antibody is approximately 200 kilo daltons, and said enzyme-linked antibody is prereacted with an antigen (now molecular mass is approximately 200 kD) the patient antigen (20 kD) will require time to compete with the pre-reacted antigen bound to the enzyme-linked antibody and displace it. This is quite obvious from the following equilibria.

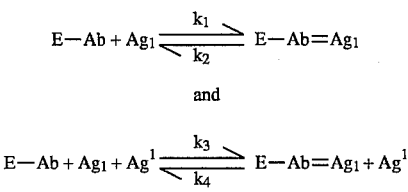

and where $k_1 = k_2$; $k_3 = k_4$ and $k_1 >> k_3$ because of steric hindrance and displacement of $Ag_1$ from E-Ab $Ag_1$ by $Ag^1$ is not easily achieved as disclosed in U.S. Pat. No. 4,446,232. Furthermore, $k3 > K4$ only if the concentration $[Ag^1] >> [Ag_1]$ that displacement will occur. This means that the amount of $Ag^1$ measured will only be at high concentrations; therefore, low sensitivity assay.

This fact is exemplified in European Patent Application No. 0 279 097 in which Fuerstenberg shows that Liotta's disclosure in U.S. Pat. No. 4,446,232 is quite insensitive as shown in Example 1 of EPA 0 279 097 for theophylline were the reflectance difference between theophylline levels of 10.4 ug/ml (therapeutic threshold) and 19.4 ug/ml (toxic threshold) is 0.55–0.43 or 0.12 units. Similarly, in Example 2 of EPA 0 279 097,200 mIU hCG was required to produce a change in color and displace the enzyme-linked hCG antibody. By all analytical standards the Liotta disclosure and the examples cited in EPA 0 279 097 using Liotta's method show that said method as disclosed in U.S. Pat. No. 4,446,232 is not sensitive enough to be a reliable analytical tool.

Other United States and foreign patent specifications and applications dealing with elements for the determination of biological fluids are cited here for completion.

U.S. Pat. Nos. 4,144,306; 4,366,241; 4,740,468; 4,774, 192; 4,632,901; 4,774,174; 4,769,333; 4,769,216; 3,811,840 and 4,042,335.

European Patent Specification Nos. 0 042 755; 0 070 300 and European Patent Applications 0 281 201; 0 284 232 and International Applications WO84/029193 and WO88/06723

SUMMARY OF THE INVENTION

Briefly, the present invention comprises a method for measuring analytes in biological fluids wherein a specific binder (Ab) to a given analyte $(Ag^1)$ is covalently immobilized on a solid phase support to which a labeled analyte $(Ag_1^*)$ is prereacted to saturate almost all binding sites on said specific binder to form an immobilized specific binder-analyte labeled complex, $\text{l-Ab} \approx Ag_1^*$, which method comprises contacting a sample of biological fluid to be analyzed with said immobilized complex wherein an analyte $(Ag^1)$, if present in said sample, competes with the labeled analyte $(Ag_1^*)$ bound to the immobilized binder for binding sites on said binder thus displacing a given amount of labeled analyte $(Ag_1^*)$ which is directly proportional to the amount of analyte $(Ag^1)$ present in the sample.

This invention also comprises a diagnostic device for measuring analytes in samples of biological fluids which comprises:

a column-type assembly defining a fluid pathway having an open end adapted to receive a sample of biological fluid to be analyzed, said fluid pathway being bridged by a first solid phase support, and an effluent discharge point on the side of said support opposite said open end, a sleeve-type container having an open end and a closed end, said assembly being received in said open end of said sleeve-type container, a specific binder (Ab) covalently immobilized on said solid phase support to which an analyte label $(Ag_1^*)$ is prereacted to saturate almost all binding sites on said binder to form a first solid phase specific binder-analyte label complex, $\text{l-Ab} \approx Ag_1^*$, said solid phase complex when contacted with a biological fluid sample containing a specific analyte $(Ag^1)$, being adapted to have displaced therefrom labeled analyte $(Ag_1^*)$ in an amount directly proportional to the concentration of $Ag^1$, a second solid support, spaced apart from first solid phase support, housed at the closed end of said sleeve-type container and in proximity to said effluent discharge point, said second solid support, when contacted by the displaced labeled analyte $(Ag_1^*)$ from the effluent discharge point said first solid phase complex, being adapted to produce a visible color on said second solid support either directly or after the addition to said second solid support a substance capable of reacting with the analyte label to produce a visible color.

In accordance with the present invention a method and diagnostic device are disclosed for the determination of analytes in biological fluids wherein a specific binder for a specific analyte is covalently immobilized onto a solid support, preferably microparticles but not restricted to same, to which a labeled specific analyte is pre-reacted whereby all binding sites on the specific binder are completely occupied with the labeled analyte and in certain instances the binding sites are saturated with a combination of the labeled analyte and unlabeled analyte. Determination of a given analyte proceeds according to the following, preferred but not restricted to, analytical steps: (a) admixing a biological sample, suspected of containing a given analyte, with a diluent in a separate tube; (b) pouring the analyte/diluent mixture onto a diagnostic device, as illustrated in the drawings, whereby the analyte/diluent is contacted with the immobilized binder-analyte label complex; (c) the resultant reaction mixture flowing through the solid phase microparticle bed is contacted with a substrate specific for the displaced label and a colored product is developed in which is directly proportional to the amount of analyte present in the sample.

The affinity of a specific analyte to its specific binder is higher than the affinity of the specific analyte-label to the given binder.

DETAILED DESCRIPTION OF THE INVENTION

Turning to the drawings,

FIG. 3 is a sectional view of the device of this invention showing the elements of FIGS. 1 and 2 as fully assembled and ready to receive a sample of biological fluid at the top or open end.

FIG. 4 is a top plan view of the device of FIG. 3.

Figure 1:
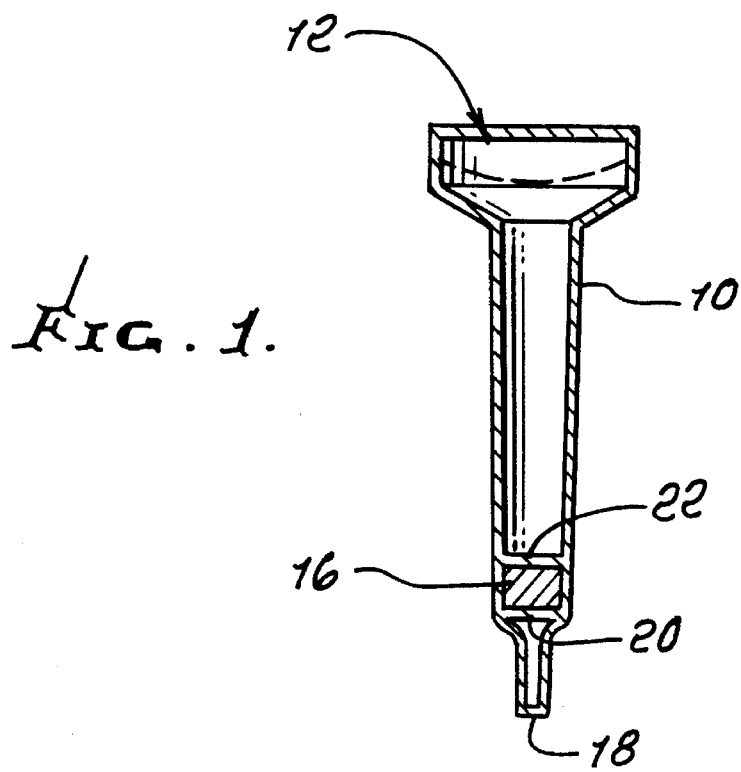
FIG. 1 is a side plan view of the column assembly present in the device of this invention.

Turning to the drawings in more detail, the method of the present invention is conducted in a novel self-contained diagnostic device in which a specific binder is covalently immobilized on microparticles and reacted with a specific labeled analyte and placed in a column assembly 10 which includes a chromatographic-type compartment. The assembly 10 has an open end 12 to receive the sample of biological fluid to be analyzed. The fluid pathway 14 runs longitudinally of the assembly 10. The solid phase support 16 bridges the assembly 10. An effluent discharge point 18 is at the lower end. The solid phase support 16 separated by two O-ring type frits 20 and 22 made of a porous substance. The assembly of FIG. 1 has a funnel-shaped cross-section and is inserted in an opaque outer-sleeve type container 24 shown in FIG. 2 that houses a 1 cm porex-type material 26 inserted at the bottom of the outer-sleeve 24. The porex-type material 26 is used to absorb excess sample/diluent volume. The base 28 of the outer-sleeve 24 is also opaque but contains in the center of it a thin (approximately 10 mm) clear white absorbant element 30 wherein the displaced labeled analyte is concentrated either through simple absorption and/or through a secondary immunological reaction involving label-antilabel or analyte-ligand antiligand. The colored product of the label is thus formed on the surface of clear absorbent 30 either through direct reading of the label, in the case where the label is a colored dye or a colored latex particle, or through the reaction of the label with its substrate, in the case where the label is an enzyme, or through the reaction of the label with its enzyme, in the case where the label is a substrate.

It is to be understood that the open end 32 of the outer sleeve 24 may be provided with a sealing cap or closure held by a force or interference fit.

Certain conditions have to be met in order to achieve maximum sensitivity for a given analyte when measured by the method of the instant invention. The following conditions are set forth to fulfill the requirements of the present invention: Reactions (1) and (2) below describe the equilibria involved in such a method

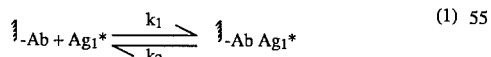
(1)

and

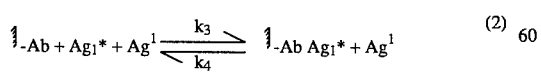
(2)

where $\}\text{-Ab}$ is the specific analyte binder covalently immobilized on solid support $Ag_1^*$ is the labeled analyte $Ag^1$ is the unlabeled analyte to be measured.

The affinity constant for reaction (1) above is $$K_1; K_1 = \frac{k_2}{k_1}$$

$K_2 > k_1$, i.e. the labeled analyte should have a fairly high affinity to the specific analyte binder and the reaction is always favored to the direction of the binder-analyte label complex where $$K1 = \frac{k_2}{k_1}.$$

The affinity constant for reaction (2) above is $$K^1; K^1 = \frac{k_4}{k_3}$$

$K_3 > k_4$, i.e. the analyte should have a higher affinity to the specific binder than does the labeled analyte, thus $K_3 > k_1$. In other words, the affinity of the unlabeled analyte to the analyte's specific binder is at least about $10^7$ $1/\text{mol}$ and should be greater than the label analyte has to the same binder.

For large molecular mass analytes (>20 kD) $k_3$ could be made greater than $k_4$ by two different analytical manipulations, either separately or combined:

1) Increasing the concentration of the enzyme labeled analyte $[Ag_1^*]$ that is bound to immobilized specific binder in reaction (1), supra, to a point of maximum saturation wherein there exists no binding sites unoccupied on the specific binder. Therefore, shifting the equilibrium to the right in reaction (1), supra, where $k_1 > k_2$. This should be accomplished without creating a steric hindrance situation on the solid phase. This is possible by diluting the solid phase, e.g. sepharose, with sepharose that does not contain the specific binder thus spacing the immobilized specific binder entities within said solid phase matrix far apart to avoid steric hindrance.

The addition of a minimal concentration of $Ag^1$ should easily displace the label analyte $Ag_1^*$ from the immobilized specific binder; therefore, $k_3 > k_4$ and a signal is produced which is directly proportional to the concentration of added analyte $[Ag^1]$.

2) Binding sites unoccupied on the immobilized specific binder $\}$-Ab by the labeled analyte $Ag_1^*$ could cause low sensitivity assays because the addition of analyte, $Ag^1$ from a biological specimen will first bind to these unoccupied sites on the specific binder and not displace the labeled analyte. By saturating these sites with "cold" analyte prior to the assay, the addition of analyte from a biological specimen will displace enzyme labeled analyte at low concentrations, thus a high sensitivity assay especially since $k_1 > k_2$ as explained, supra. A combination of 1 and 2, supra, could even yield sensitivities in the sub-nanogram range as will be shown in the instant examples of the invention.

Multiple analytes could be screened using the method and diagnostic device of the present invention by admixing several immobilized specific binders to various analytes in their respective appropriate dilutions; thus, the solid phase support will contain multiple specific binders to which a specific analyte-labeled has been pre-reacted and stabilized $$\}\text{-Ab}_1 \approx Ag_1^*$$

∫-Ab$_2$≈Ag$_2$*

∫-Ab$_3$≈Ag$_3$*

∫-Ab$_n$≈Ag$_n$* where ∫-Ab$_1$ to ∫-Ab$_n$ are various immobilized specific binders to which a specific analyte-labeled Ag$_1$* to Ag$_n$* have been prereacted and stabilized. The mixture containing the various immobilized pre-reacted specific binders-analyte labels could now serve as one reagent for screening several analytes in one give specimen without any loss of sensitivity. This is particularly useful for drug screening programs where multiple drugs could be screened on a given specimen. A positive result using said multiple approach could then be confirmed using the single analyte approach.

Screening for other types of analytes using the disclosed invention should be obvious to those skilled in the art.

In the following examples the conjugation and labeling methods used are well-known in the art and are presented here for illustrative purposes only and should not be restrictive to the practice of the instant invention. Other conjugation and labeling procedures could easily be used by those skilled in the art. Furthermore, the type of solid phase used to immobilize the analyte's specific binder and the type of enzyme or other label used are not restrictive and are obvious to those skilled in the art.

The analyte's specific binders used in the following examples were antibodies, polyclonal or monoclonal, raised against various analytes. The analyte's specific IgG from these various antibodies was routinely purified by Protein-A chromatography using immobilized recombinant protein-A (Repligen, Cambridge, Mass. 02139) following well-known established procedures.

The Protein-A purified specific IgG was covalently bound to cyanogen bromide activated sepharose 4B by the method of March, C. S. et al., 1974. Anal. Biochem. 60:149–152.

Macromolecular antigens (molecular mass greater than 20 K.D.) were enzyme (horseradish peroxidase) labeled using the periodate method of Boorsma, D. M., et al (1979). J. Immunol. Meth. 30:245–255.

Haptens were coupled to horseradish peroxidase enzyme using the carbodiimide method of Staros, J. V. (1986). Anal. Biochem. 156:220–222.

The device can be built as an integral unit or alternatively elements 10 and 24 can be assembled at the time of use.

The following Examples are illustrative of the invention, and are not intended to be limiting in any way.

EXAMPLE 1

MORPHINE ASSAY IN URINE

Morphine-3-glucuronide was conjugated to horseradish peroxidase enzyme using a modification of the method of Staros et al, 1986, supra, as follows:

(1) 2.95 mg of morphine-3-glucuronide (6.4×10-3) mmol) were dissolved in 0.5 ml of normal saline to which 20 mg of horseradish peroxidase (RZ>3) dissolved in 3.0 ml of normal saline were added.

(2) 15 mg of N-hydroxysuccinimide was added to the mixture in (1) and stirred until it was dissolved to which 40 mg of EDC (N-ethyl-N-(3-dimethylaminopropyl) carbodiimide) dissolved in 0.5 ml normal saline was added dropwise over 30 minutes.

(3) The reaction mixture in (2) was stirred for an extra 60 minutes at ambient temperature and a further 10 mg EDC added as powder. The reaction mixture was stirred overnight.

(4) The enzyme conjugate was then dialyzed for 48 hours against 2×5 liters of phosphate-buffered saline and finally charcoal absorbed twice using 20 mg activated charcoal in an ice bath and filtered through 0.22 micron filter. 40 mls of morphine antibody (polyclonal) was purified on Protein A column as described, supra, to yield 378 mg IgG which was then conjugated to cyanogen bromide activated sepharose 4B as indicated to yield 3.6 mg IgG/ml of gel, and diluted at an appropriate dilution in unreacted sepharose 4B in the ratio of 1:100 (1 part morphine antibody coated gel to 100 parts unreacted sepharose gel). The working gel could be stored in phosphate-buffered saline solution containing 0.02% (w/v) sodium azide at 4° C. for extended time periods without any loss or "leakage" of IgG.

Binding of morphine-horseradish peroxidase conjugate to the solid phase morphine antibody was accomplished as follows:

The diluted morphine antibody (IgG)-sepharose gel was washed with a diluent prepared in 0.05M phosphate buffer pH 7.0 containing 0.01% (w/v) thimerosal, 0.2% (w/v) alkali treated casein, 0.1% (w/v) charcoal absorbed human serum albumin and 20 ug/ml gentamicin sulfate, and was reconstituted such that 2 ml of gel suspension in said buffer contains 1 ml of settled gel volume. The morphine-enzyme conjugate was then added to the morphine-antibody gel suspension to give a final concentration of 1:1000 and the mixture was incubated for 60 minutes at ambient temperature on a rotary mixer. This process causes the binding of morphine-enzyme label to the immobilized morphine specific antibody on the sepharose. Unbound or free enzyme conjugate is washed off the solid phase with the 0.05M phosphate buffer, pH 7.0 diluent. The washed gel containing the immobilized morphine antibody-morphine horseradish peroxidase complex is transferred to the diagnostic device (FIG. 1) as described, supra, and each device now contains 250 ul of settle gel (3, FIG. 1). Few milliliters of diluent are passed through the gel to ensure that no more enzyme elutes from the gel. The gel containing the immobilized antibody-analyte label complex could be stored at 4° C. either lyophilized or suspended in the 0.05M phosphate, pH 7.0, diluent in the diagnostic device until used.

The affinity constant of morphine to the morphine antibody was calculated by the method of J. D. Teale ("Radioimmunoassay". In David Williams, Ronald Nunn, Vincent Marks (eds), Scientific Foundations of Clinical Biochemistry, Vol. 1, 1978:299–322, Pub. William Heinemann, London) and found to be $4.0 \times 10^{11}$ 1/mol. The affinity constant of morphine-3-glucuronide to the same antibody was also calculated by the same method and found to be $8 \times 10^{10}$ 1/mol.

Description of the Working Model

Figure 2:
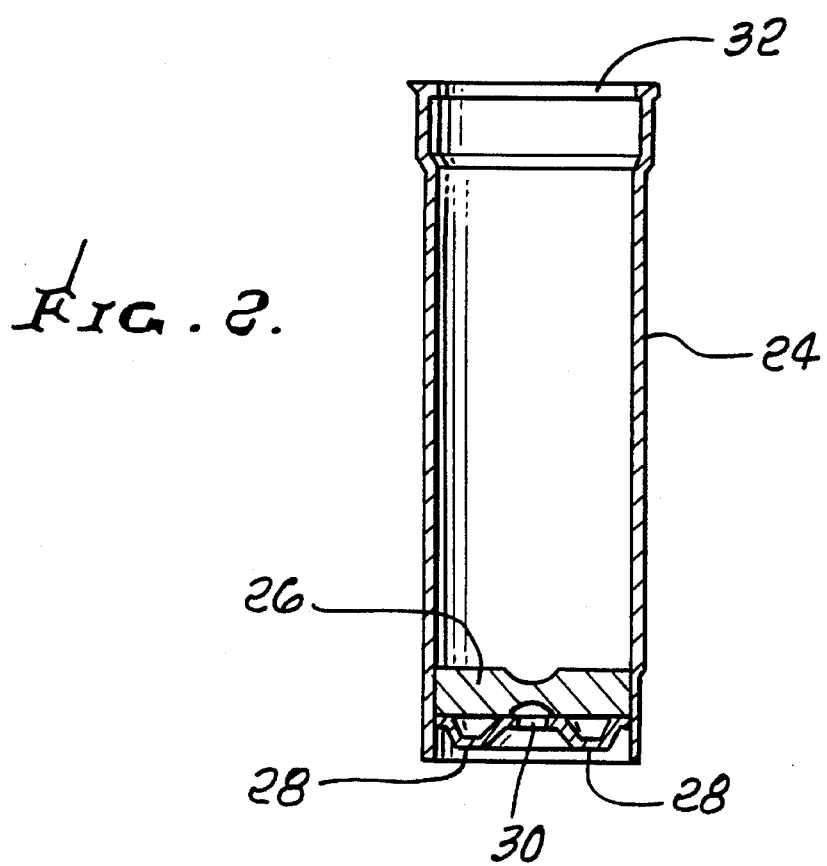
FIG. 2 is a sectional view of the sleeve-type container used in the device of this invention.

The diagnostic device once assembled will contain 250 ul of suspended gel (16) containing the immobilized antibody-analyte label complex in the column assembly 10 part of the device, FIG. 1, and protected on each side by two porous frits 20 and 22. The inner part of device, the column assembly 10, is housed in the outer-sleeve 24 shown in FIG. 2, as described, supra. 126 samples were analyzed to determine the presence or absence of morphine and/or opiates using the described diagnostic device and reagents as follows:

1. 2 drops of urine were added to 900 ul of sample dilutent (0.05 mg/ml of tetramethylbenzidine in phosphate buffered saline, pH 7.4) to give an approximate 1:10 (v/v) dilution of sample.

2. The contents of sample plus diluent were poured onto the top 12 of the diagnostic assembly 10.
3. The device was inverted and one drop of peroxide at a concentration of 0.02% in citrate/phosphate buffer, pH 5.0, was added to the clear white absorbent element (7). After 5 minutes color was observed and recorded: white=negative; blue=positive.

The results of the above assays showed that out of the 126 samples analyzed 71 samples were negative and 55 were positive. When compared against a sensitive RIA assay for morphine (Coat-a-Count Morphine kit Diagnostic Products Corporation, Los Angeles, Calif. 90045) 100% agreement was achieved. The positive samples had morphine RIA values ranging from 162 ng/ml to 116,200 ng/ml. All 71 negative samples were from known volunteers not taking any drugs.

The Coat-a-Count RIA assay had a cut-off of 25 ng/ml for free morphine. The morphine assay of the present invention is set at a cut-off of 300 ng/ml for morphine-3-glucuronide and 50 ng/ml cut-off for free morphine. Levels below 300 ng/ml of morphine-3-glucuronide or 50 ng/ml free morphine will not produce any visible color.

The following compounds did not produce any visible color when assayed in the morphine method of the present invention at concentrations of 10,000 ng/ml:

oxazepam cotinine caffeine acetaminophen

PCP acetylsalicylic acid secobarbital amphetamine cocaine fentanyl

LSD bupreneorphine lidocaine ibuprofen fenfluramine

D-propoxyphene methaqualone benzoylecogonine methadone

EXAMPLE 2

PHENCYCLIDINE (PCP) ASSAY IN URINE

Phencyclidine (PCP) derivative, 1-[1-(phenyl-3-O-carboxymethyl ether)-cyclohexyl]piperidine, synthesized according to the methods of Kalir, A., et al, 1969, J.Med. Chem. 12:473 and Rao, P. N. et al, 1980, J. Steroid Biochem, 13:1291, was conjugated to horseradish peroxidase by the method of Staros, et al 1986, supra, as outlined in Example 1, supra, except that the PCP derivative was dissolved in dimethylformamide instead of normal saline.

20 mls of PCP antibody (polyclonal) were purified on Protein A column as described, supra, to yield 254 mg IgG which was then conjugated to cyanogen bromide activated sepharose 4B as indicated to yield 1.3 mg IgG/ml of gel and diluted at an appropriate dilution in unreacted sepharose 4B in the ratio of 1:5 (1 part PCP antibody coated gel to 5 parts unreacted sepharose gel). The diluted gel is stored as indicated in Example 1, supra. PCP-horseradish peroxidase conjugate was bound to the PCP antibody diluted gel after a dilution of 1:1000 in the phosphate buffer, pH 7.0, diluent as described under Example 1, supra. The gel containing the immobilized PCP antibody-PCP horseradish peroxidase label was first washed with 0.02M citrate/acetate buffer, pH 5.0, then rewashed with phosphate buffer, pH 7.0, diluent to remove unbound or free enzyme conjugate. The washed pre-reacted gel was transferred to the diagnostic devices, as in Example 1, supra.

The affinity constants of PCP and horseradish peroxidase PCP to the PCP antibody were calculated by the method of Teale, 1978, supra, and were determined to be $1.4 \times 10^{12}$ $1$/mol for PCP and $3.0 \times 10^{10}$ $1$/mol for horseradish eproxidase-PCP conjugate.

Seventy-one urine specimens were analyzed for PCP using the described reagents and diagnostic device of the present invention, as indicated for morphine in Example 1, supra, and compared to a sensitive RIA PCP method (Coat-a-Count PCP, Diagnostic Products Corporation, Los Angeles, Calif. 90045).

50 samples were from known PCP addicts and were RIA positive at a cut-off of 25 ng/ml. All 50 samples were also positive by the method of the instant invention at a cut-off of 50 ng/ml. All 21 negative samples were correctly identified.

The positive samples had PCP RIA values ranging from 151 ng/ml to 2672 ng/ml.

The following drugs gave negative results, no visible color, when assayed in the PCP method of the present invention at concentrations of 10,000 ng/ml Ethyl morphine morphine methaqualone cotinine secobarbital lidocaine normorphhine diazepan D-propoxyphene phenobarbital acetominophen acetylsalicylic acid amphetamine benzoylecgonine bupreneorphine caffeine ecgonine codeine.

The following drugs gave positive results (equivalent to 100 ng/ml PCP) at the concentrations indicated:

| | |
|---|---|
| 1-[1-(2-Thienyl)-cyclohexyl] piperidine | 100 ng/ml |
| 1-(1-Phenylcylcohexyl)-4-hydroxypiperidine | 1000 ng/ml |
| N-Ethyl Phencyclidine | 10,000 ng/ml |

EXAMPLE 3

URINARY HUMAN ALBUMIN ASSAY

Human albumin was conjugated to horseradish peroxidase by the periodate method of Boorsma et al, 1979, supra.

Monoclonal antibody rasised against human albumin was prepared according to the method of Galfre, G. and Milstein, C. (Preparation of Monoclonal Antibodies: Strategies and Procedures. In Methods of Enzymology, Immunochemical Techniques, vol. 73, Langone, J. and Van Vunakis, H., eds. Academic Press (1981) pp. 3–46).

The ascites fluid was purified on Protein A column as described, supra, and the affinity of the monoclonal antibody to human albumin was $2.3 \times 10^7$ l/mol as determined by the method of Adrion, R. F. 1982, Clin. Chem. (lett); 28, p. 717. The monoclonal specific IgG was coupled to Sepharose 4B by the cyanogen bromide activation procedure of March et al, 1974, supra, to yield 0.763 mg IgG/ml of gel. The IgG coupled gel was diluted with casein-coupled Sepharose 4B (4.92 mg casein/ml of gel), using the same coupling procedure as that for IgG, in various ratios described below. The diluted gel containing the human albumin monoclonal antibody was then reacted with human albumin-horseradish peroxidase conjugate for 1 hour at ambient temperature and washed with the phosphate buffer, pH 7.0, diluent as described in Example 1, supra. The washed gel now containing immobilized human albumin monoclonal antibody-human albumin-horseradish peroxidase $\}$-$Ab_{HA}$≈HA-E) was then reacted with 300 ug/ml human albumin equivalent (30 ug albumin per 250 ul of gel) to saturate all binding sites on the albumin monoclonal antibody. The gel is rewashed with the phosphate buffer, pH 7.0, diluent to remove any unreacted "cold" albumin and transferred to the diagnostic device of the present invention. To check the effective minimum detection level for measuring albumin in urine using the above-described method, urinary albumin calibrators containing 10, 20, 30 and 40 ug/ml of albumin were diluted 1:10 in the sample diluent (0.05 mg/ml of tetramethylbenzidine in phosphate buffered saline, pH 7.4) as described under Example 1, supra, and applied to diagnostic devices containing the following ratios of reagents as shown in Table 1.

TABLE 1

|   | $\}$-IgG gel | $\}$-CASEIN gel | Albumin-HRPO Dilution | "Cold" Albumin ug per 250 ul gel | Minimum Detection Limit ug/ml |
|---|---|---|---|---|---|
| DEVICE 1 | 1 part | 25 parts | 1:100 | 30 | 20 |
| 2 | 1 part | 50 parts | 1:25 | 30 | 40 |
| 3 | 1 part | 50 parts | 1:50 | 30 | 20 |
| 4 | 1 part | 25 parts | 1:200 | 30 | 20 |
| 5 | 1 part | 50 parts | 1:100 | 30 | 20 |
| 6 | 1 part | 50 parts | 1:50 | 0 | 320 |
| 7 | 1 part | 25 parts | 1:25 | 0 | 340 |

Thus, saturating the unoccupied binding sites by manipulating the albumin-enzyme conjugate and the addition of "cold" albumin enable the system to detect 20 ug/ml of urinary albumin. Without the added "cold" albumin the detection limit is approximately 330 ug/ml. Published studies (Mogensen, 1984, supra) based on highly sensitive RIA for albumin have established the upper limit of normal for adults as approximately 15 ug/minute or approximately 17 ug/ml (based on 1600 mls of urine is excreted in 24 hour period) and a range extending from 20–30 ug/ml to about 150 ug/ml as an operational definition of microalbuminuria. The disclosed methods of the present invention allows the rapid detection of albumin in urine at levels only previously achieved with highly sensitive immunoassays.

EXAMPLE 4

URINARY HUMAN CHORIONIC GONADOTROPIN (hCG)

hCG was conjugated to horseradish peroxidase by the periodate method of Boorsma et al., 1979, supra.

Monoclonal antibody raised against hCG was prepared according to the method of Galfre et al, 1981, supra.

The ascites fluid was purified on Protein A column as described, supra, and the affinity of the monoclonal specific antibody to hCG was $1.18 \times 10^9$ l/mol as determined by the method of Adrion, R. F. 1982, supra. The monoclonal specific IgG was coupled to Sepharose 4B by the cyanogen bromide activation procedure of March et al, 1974, supra, to yield 0.95 mg IgG/ml. The IgG coupled gel was diluted with unreacted Sepharose 4B in ratio of 1:25 (1 part IgG gel to 25 parts unreacted Sepharose 4B). The diluted gel containing hCG monoclonal antibody was then reacted with hCG-horseradish peroxidase conjugate dilute 1:25 in phosphate buffer, pH 7.0, diluent for 4 hours at ambient temperature and washed with phosphate buffer, pH 7.0, diluent as described in Examples 1 and 3, supra.

The washed gel now containing immobilized hCG monoclonal antibody-hCG-horseradish peroxidase $\}$-$Ab_{hCG}$≈hCG-E) was then reacted with various amounts of "cold" hCG to saturate all binding sites on the hCG monoclonal antibody as shown in Table 2 below. The gel was re-washed with phosphate buffer, pH 7.0, diluent to remove any unreacted "cold" hCG and transferred to the diagnostic device of the present invention.

The minimum detection level for measuring hCG in urine using the above-described method, was checked by using urinary hCG calibrators containing 20, 30, 40, 50 and 60 mIU/ml of hCG diluted 1:10 in the sample diluent as described under Examples 1–3, and applied to diagnostic devices containing the following reagent ratios as shown in Table 2.

TABLE 2

|   | $\}$-IgG gel | $\}$-CASEIN gel | hCG-HRPO Dilution | "Cold" hCG mIU per 250 ul gel | Minimum Detection Limit mIU/ml |
|---|---|---|---|---|---|
| DEVICE 1 | 1 part | 25 parts | 1:25 | 0 | 60 |
| 2 | 1 part | 25 parts | 1:25 | 1 | 50 |
| 3 | 1 part | 25 parts | 1:25 | 2 | 40 |
| 4 | 1 part | 25 parts | 1:25 | 3 | 30 |
| 5 | 1 part | 25 parts | 1:25 | 4 | .020 |

The effective minimum detectable limit for the urinary hCG assay is approximately 20 mIU/ml. Without the added "cold" hCG the detection limit is approximately 60 mIU/ml. Meticulous titering of "cold" hCG in the system could yield sensitivities even lower than 20 mIU/ml.

Having fully described the invention it is intended that it be limited solely by the lawful scope of the appended claims:

1. A method for measuring analytes in biological fluids which comprises:
   (1) covalently immobilizing a specific antibody binder to a given analyte on a solid phase support;
   (2) saturating the binding sites on said specific antibody binder with a labeled analyte to the extent steric hinderance permits to form an immobilized specific antibody binder-analyte labeled complex;
   (3) saturating remaining unoccupied binding sites on the immobilized specific antibody binder-analyte labeled complex with unlabeled analyte prior to contacting said complex with a biological specimen;
   (4) contacting a sample of biological fluid to be analyzed for the presence of the given analyte with said immobilized complex, said sample of biological fluid as contacted with said immobilized complex being in an untreated form as obtained from the donor; and
   (5) and allowing an analyte, if present in said sample, to compete with the labeled analyte bound to the immobilized binder for binding sites on said binder thus displacing a given amount of labeled analyte which is directly proportional to the amount of analyte present in the sample, wherein the affinity of the analyte to the analyte's specific binder is at least about $10^7$ l/mol and is higher than the affinity of the labeled analyte to the same binder and wherein the analyte has a molecular weight greater than 20 kD.

2. The method of claim 1 wherein the displaced labeled analyte is then detected by contact with a solid support which is adapted to produce a visible color directly or after the addition to said solid support of a substance capable of reacting with the labeled analyte to produce a visible color.

3. The method according to claim 1 wherein multiple immobilized specific antibody binders are pre-reacted with their respective analyte labels to form multiple immobilized specific antibody binder-analyte labeled complexes and admixed together to serve as a single solid phase complex for screening multiple analytes in one given specimen.

4. The method according to claim 1 wherein the specific antibody binder is a polyclonal antibody raised against a given antigen or hapten.

5. The method according to claim 1 wherein the specific antibody binder is a monoclonal antibody raised against a given antigen or hapten.

6. The method according to claim 1 wherein the label is an enzyme.

7. The method according to claim 1 wherein the label is a substrate.

8. The method according to claim 1 wherein the label is a colored dye.

9. The method according to claim 1 wherein the label is a colloidal gold.

10. The method according to claim 1 wherein the label is a colored dye entrapped in a liposome.

11. The method according to claim 1 wherein the label is a pH indicator.

12. The method according to claim 1 wherein the solid phase support is an activated insoluble cross-linked carbohydrate polymer gel.

13. The method according to claim 1 wherein the solid phase support is an activated polymer microsphere latex particle.

14. The method according to claim 1 wherein the solid phase support is an activated controlled pore-size glass particle.

15. The method according to claim 1 wherein the solid phase support is an activated cellulose particle or nitrocellulose particle.

16. A method for measuring analytes in biological fluids which comprises:
   (1) covalently immobilizing a specific lectin binder to a given analyte on a solid phase support;
   (2) saturating the binding sites on said specific lectin binder with a labeled analyte to the extent steric hinderance permits to form an immobilized specific lectin binder-analyte labeled complex;
   (3) saturating remaining unoccupied binding sites on the immobilized specific lectin binder-analyte labeled complex with unlabeled analyte prior to contacting said complex with a biological specimen;
   (4) contacting a sample of biological fluid to be analyzed for the presence of the given analyte with said immobilized complex, said sample of biological fluid as contacted with said immobilized complex being in an untreated form as obtained from the donor; and
   (5) and allowing an analyte, if present in said sample, to compete with the labeled analyte bound to the immobilized binder for binding sites on said binder thus displacing a given amount of labeled analyte which is directly proportional to the amount of analyte present in the sample, wherein the affinity of the analyte to the analyte's specific binder is at least about $10^7$ l/mol and is higher than the affinity of the labeled analyte to the same binder, and wherein the analyte has a molecular weight greater than 20 kD.

* * * * *